US012588873B2

(12) United States Patent
Nichol et al.

(10) Patent No.: US 12,588,873 B2
(45) Date of Patent: Mar. 31, 2026

(54) ANIMAL CARE AND MONITORING PLATFORM

(71) Applicant: Brisby, Inc., Newton, MA (US)

(72) Inventors: Jamie Gordon Nichol, Carlisle, MA (US); Neil Stepak, Vancouver (CA); Mark Florence, Newton, MA (US)

(73) Assignee: Brisby, Inc., Newton, MA (US)

( * ) Notice: Subject to any disclaimer, the term of this patent is extended or adjusted under 35 U.S.C. 154(b) by 196 days.

(21) Appl. No.: 17/412,996

(22) Filed: Aug. 26, 2021

(65) Prior Publication Data

US 2022/0061765 A1 Mar. 3, 2022

Related U.S. Application Data

(60) Provisional application No. 63/071,181, filed on Aug. 27, 2020.

(51) Int. Cl.
*A61B 5/00* (2006.01)
*A61B 5/01* (2006.01)
(Continued)

(52) U.S. Cl.
CPC .......... *A61B 5/6891* (2013.01); *A61B 5/0008* (2013.01); *A61B 5/01* (2013.01); *A61B 5/024* (2013.01); *A61B 5/0816* (2013.01); *A61B 5/48* (2013.01); *A61B 2503/40* (2013.01); *A61B 2560/0252* (2013.01); *A61B 2562/0271* (2013.01)

(58) Field of Classification Search
CPC ......... A61B 5/0008; A61B 5/01; A61B 5/024;

A61B 5/0816; A61B 2503/40; A61B 2560/0252; A61B 2562/0271; A01K 1/0353; A01K 29/005

See application file for complete search history.

(56) References Cited

U.S. PATENT DOCUMENTS 4,136,497 A * 1/1979 Porter ..................... E04C 2/205
52/483.1
8,672,842 B2 3/2014 Kenalty et al.
(Continued)

FOREIGN PATENT DOCUMENTS

DE 20003211 U1 5/2000
EP 3264299 A1 1/2018
(Continued)

OTHER PUBLICATIONS

[No Author Listed] PETKIT, retreived from the Internet under www.petkit.com, on Mar. 21, 2021, home page attached, 3 pages.
(Continued)

*Primary Examiner* — Carl H Layno
*Assistant Examiner* — Maria Catherine Anthony
(74) *Attorney, Agent, or Firm* — Nutter McClennen & Fish LLP

(57) ABSTRACT

A smart animal bed system includes a base supporting a padded animal bed; a movement sensor for providing movement sensor signals in response to movement of an animal within the padded animal bed; and a temperature control system having a heating mode and a cooling mode, the temperature control system configured to selectively provide heating or cooling to the padded animal bed based at least in part on the movement sensor signals.

25 Claims, 15 Drawing Sheets

(51) Int. Cl.
    *A61B 5/024*      (2006.01)
    *A61B 5/08*       (2006.01)

(56)             References Cited

U.S. PATENT DOCUMENTS

| | | | |
|---|---|---|---|
| 10,477,978 B1 | 11/2019 | Youngblood et al. | |
| 2008/0022935 A1 * | 1/2008 | Fine | A01K 1/0353 |
| | | | 119/28.5 |
| 2016/0136385 A1 * | 5/2016 | Scorcioni | A61B 5/4812 |
| | | | 600/26 |
| 2019/0281331 A1 | 9/2019 | Tang | |
| 2020/0345971 A1 * | 11/2020 | Schirm | A61F 7/02 |

FOREIGN PATENT DOCUMENTS

| | | | | |
|---|---|---|---|---|
| GB | 2447287 A | 9/2008 | | |
| KR | 20160102296 A * | 8/2016 | | A61B 5/01 |
| KR | 20190136141 A | 12/2019 | | |
| WO | 2018016702 A1 | 1/2018 | | |
| WO | 2020/089704 A1 | 5/2020 | | |

OTHER PUBLICATIONS

[No Author Listed] VARRAM, retrieved from the Internet under www.varram.com, on Mar. 21, 2021, home page attached, 13 pages.
[No Author Listed] VERTRAX, retrieved from the Internet under www.vetrax.com, on Mar. 21, 2021, home page attached, 5 pages.
[No Author Listed] PAWBOT, retrieved from the Internet under https://pawbot.com/, on Mar. 21, 2021, home page attached, 3 pages.
[No Author Listed] Meet Paw Bot—Automated Cat & Dog wet food dispenser—Kickstarter Apr. 28, 2017, retrieved from the internet under https://www.kickstarter.com/projects/pawbot/automatic-wet-food-dispenser-cats-dogs-18-cans-paw/ on Mar. 21, 2021, home page attached, 10 pages.
[No Author Listed] "Automatic Wet Cat Food dispenser| PawBot | 18 cans capacity | Multi Day." Jan. 13, 2017, retrieved from the Internet under https://youtu.be/W_cgH4HUI8E, on Mar. 21, 2021, 1 page.
International Search Report and Written Opinion of the International Searching Authority for Application No. PCT/US2021/047746, mailed Dec. 15, 2021 (11 pages).
European Search Report, Extended European Search Report for Application No. 21862734.7 dated Aug. 1, 2024 (9 pages).

* cited by examiner

201

202

203

307

506

504

506

601

602

B

B

603

604

605

606

602

502

503

505

501

SECTION B - B

1301

1401

SECTION A - A

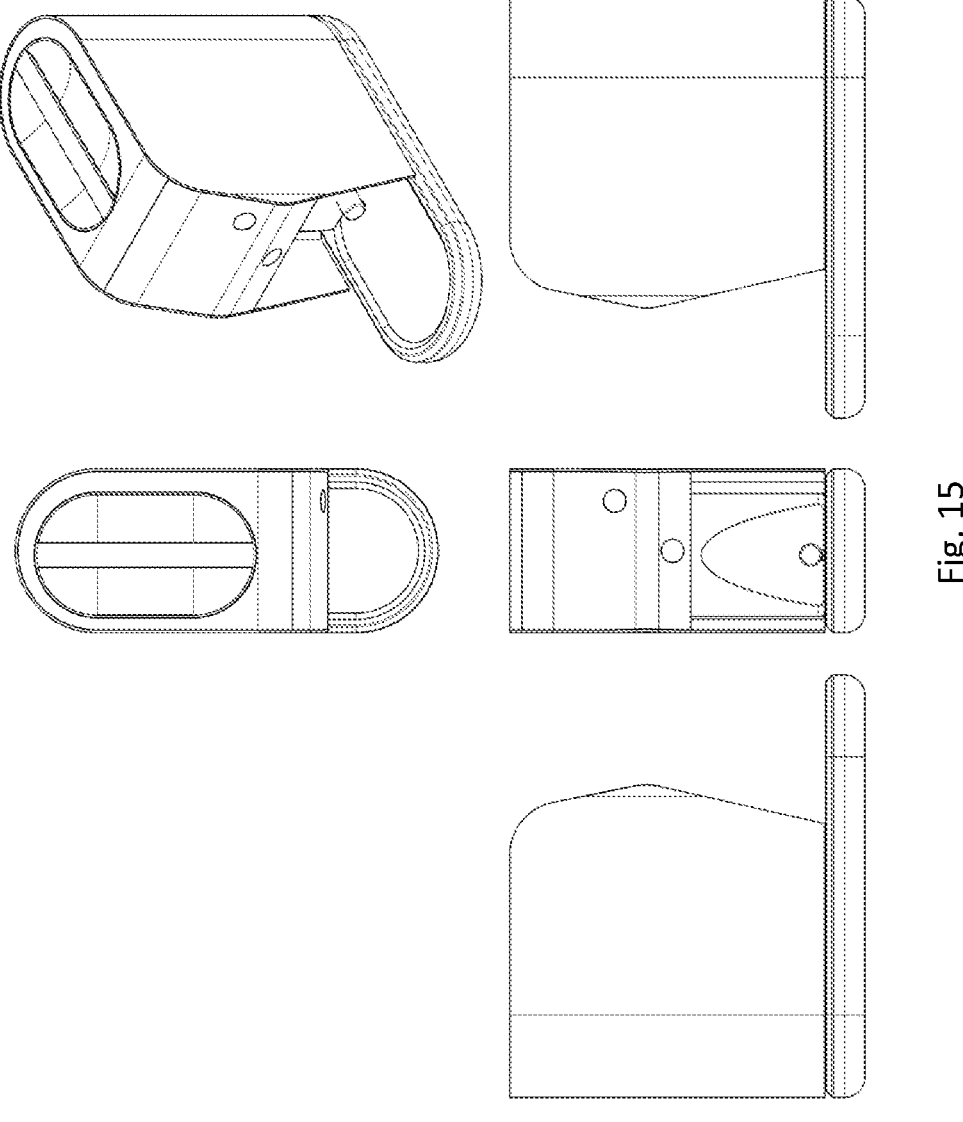
Fig. 15
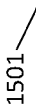
1501

ANIMAL CARE AND MONITORING PLATFORM

CROSS-REFERENCE TO RELATED APPLICATION(S)

This patent application claims the benefit of U.S. Provisional Patent Application No. 63/071,181 entitled ANIMAL CARE AND MONITORING PLATFORM filed Aug. 27, 2020, which is hereby incorporated herein by reference in its entirety.

FIELD

The present disclosure relates to an animal care and behavioral monitoring platform, and computing platform for the collection, integration, analysis and reporting of animal-related information.

SUMMARY OF VARIOUS EMBODIMENTS

In accordance with one embodiment of the invention, a smart animal bed system comprises a base having a padded animal bed; at least one sensor for providing sensor signals indicative of a condition of the animal within the padded animal bed; and a temperature control system having a heating mode and a cooling mode operated by a controller, the temperature control system configured to selectively provide heating or cooling to the padded animal bed based at least in part on the sensor signals.

In various alternative embodiments, the at least one sensor may include a piezoelectric sensor such as for monitoring movement, vital signs, and/or weight of the animal, a temperature sensor such as for monitoring temperature of the animal or animal bed, and/or an ambient temperature sensor such as for monitoring an ambient temperature (e.g., room or outside temperature).

In certain exemplary embodiments, the temperature control system may include a thermally conductive gel-padded surface coupled to a heat sink. The thermally conductive gel-padded surface may be affixed to a thermally conductive baseplate that in turn is coupled to the heat sink. The thermally conductive baseplate may include a thermal insulator (e.g., foam insulation) such as on a bottom surface. The thermally conductive baseplate may be coupled to the heat sink via a set of thermoelectric heat pump devices (e.g., Peltier devices), with each thermoelectric heat pump device in low-thermal-resistance contact with the baseplate and the heat sink such as via a debossed pad, which may be configured to accommodate a thermal insulator beneath the thermally conductive baseplate. Current flow through the thermoelectric heat pump devices in a first direction may provide cooling and current flow through the thermoelectric heat pump devices in a reverse direction may provide heating such that the controller may be configured to switch between the heating mode and the cooling mode by switching the current flow direction. The smart animal bed system typically includes a power source for providing the current flow. The smart animal bed system may include one or more fans for drawing heat from the heat sink.

In certain other embodiments, the temperature control system may include at least one conduit through which heated fluid is circulated in the heating mode and through which cooled fluid is circulated in the cooling mode, e.g., through a thermally regulated zone of the padded animal bed. The system may include a liquid reservoir for holding liquid to be heated or cooled and may include a thermoelectric element for selectively heating and cooling the liquid and/or a pump for circulating the fluid through the at least one conduit.

Generally speaking, the controller may ascertain a condition of the animal based on the sensor signals and may control the temperature of the padded animal bed based on the condition. The condition may include respiration rate, heart rate, resting or inactivity time, crying, temperature, restlessness, nervousness, and/or other conditions. The system may include an ambient temperature sensor for providing ambient temperature signals, in which case the temperature control system may be configured to selectively provide heating or cooling to the padded animal bed based at least in part on the condition and the ambient temperature signals. In various alternative embodiments, the controller may be integral to the base having the padded animal bed or may be separate from the base having the padded animal bed (e.g., a cloud-based controller) with the controller receiving the sensor signals over a communication system (e.g., which may include the Internet) and providing control signals to the temperature control system over the communication system.

Additional embodiments may be disclosed and claimed.

BRIEF DESCRIPTION OF THE DRAWINGS

The accompanying drawings, which are included to provide a better understanding of the disclosure, illustrate embodiment(s) of the disclosure and together with the description serve to explain the principle of the disclosure. In the drawings:

FIG. 15 illustrates a smart water dispenser in accordance with the present disclosure.

DETAILED DESCRIPTION

Various embodiments are described more fully hereinafter with reference to the accompanying drawings, in which one or more exemplary embodiments of the invention are shown. Like numbers used herein refer to like elements throughout. This invention may, however, be embodied in many different forms and should not be construed as limited to the embodiments set forth herein; rather, these embodiments are provided so that this disclosure will be operative, enabling, and complete. Accordingly, the particular arrangements disclosed are meant to be illustrative only and not limiting as to the scope of the invention, which is to be given the full breadth of the appended claims and any and all equivalents thereof. Moreover, many embodiments, such as adaptations, variations, modifications, and equivalent arrangements, will be implicitly disclosed by the embodiments described herein and fall within the scope of the present invention.

Although specific terms are employed herein, they are used in a generic and descriptive sense only and not for purposes of limitation. Unless otherwise expressly defined herein, such terms are intended to be given their broad ordinary and customary meaning not inconsistent with that applicable in the relevant industry and without restriction to any specific embodiment hereinafter described. As used herein, the article "a" is intended to include one or more items. Where only one item is intended, the term "one", "single", or similar language is used. When used herein to join a list of items, the term "or" denotes at least one of the items but does not exclude a plurality of items of the list.

For exemplary methods or processes of the invention, the sequence and/or arrangement of steps described herein are illustrative and not restrictive. Accordingly, it should be understood that, although steps of various processes or methods may be shown and described as being in a sequence or temporal arrangement, the steps of any such processes or methods are not limited to being carried out in any particular sequence or arrangement, absent an indication otherwise. Indeed, the steps in such processes or methods generally may be carried out in various different sequences and arrangements while still falling within the scope of the present invention.

Additionally, any references to advantages, benefits, unexpected results, or operability of the present invention are not intended as an affirmation that the invention has been previously reduced to practice or that any testing has been performed. Likewise, unless stated otherwise, use of verbs in the past tense is not intended to indicate or imply that the invention has been previously reduced to practice or that any testing has been performed.

Figure 1:
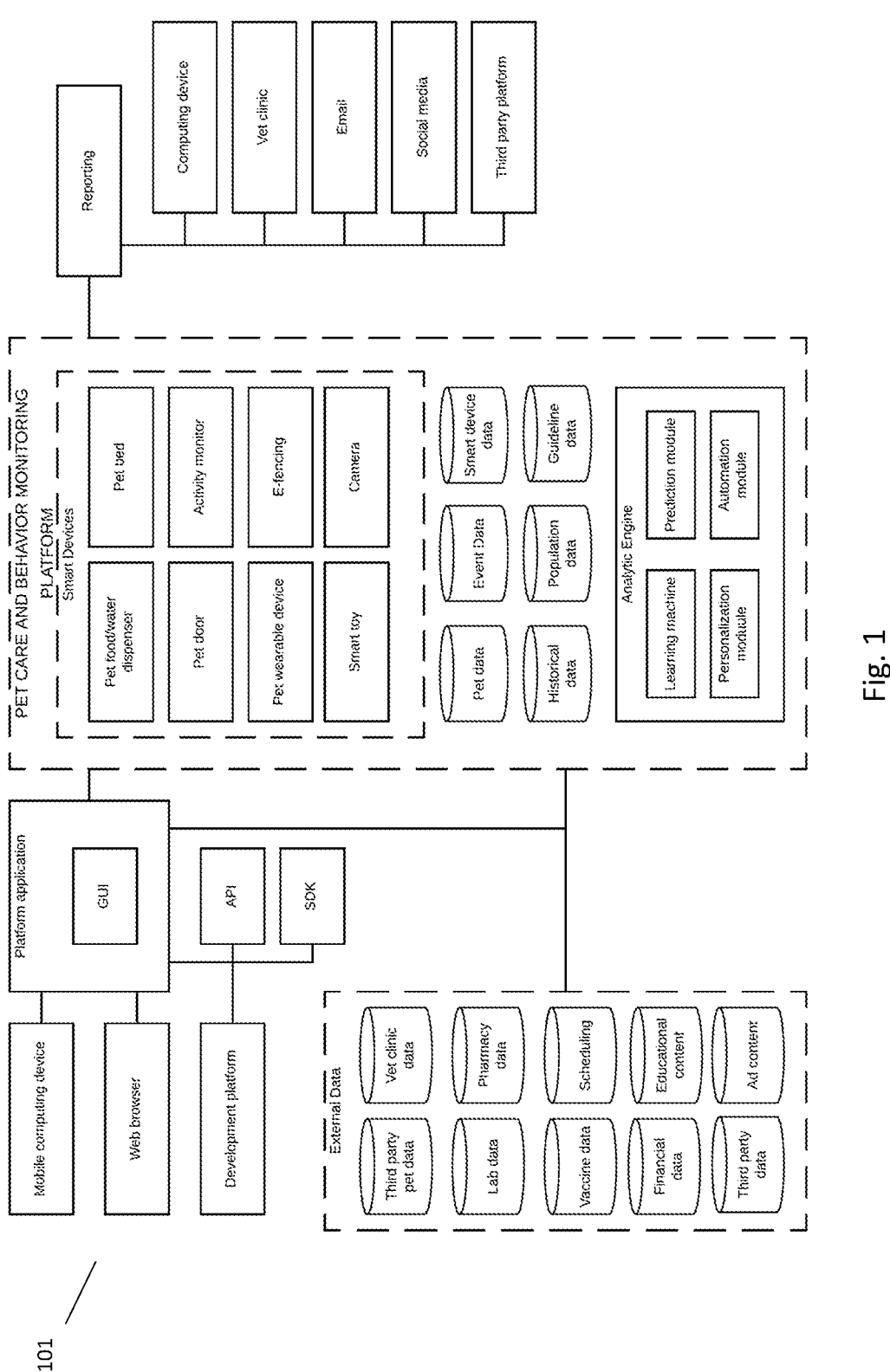
FIG. 1 illustrates a schematic overview of a platform for animal care and behavioral monitoring in accordance with the present disclosure.

The present disclosure relates to a platform 101 for animal care and behavioral monitoring as shown in FIG. 1. The platform 101 may include or connect with a plurality of smart animal devices, including but not limited to an animal food dispenser, animal water dispenser, animal bed, animal door, animal activity monitor, a wearable device for animals (e.g., smart collar), electronic fencing equipment, smart animal toys, a camera or security system, or some other type of smart device that may be operably connected to the platform 101. As appropriate, the smart animal devices of the platform 101 may each be powered by hardwired connection to a power outlet, and/or by battery (including battery usage only as a backup power source), solar or photovoltaic cell, or some other energy source. Smart animal devices may communicate with a platform server that is operatively connected with third party servers, including but not limited to veterinary clinics, laboratories, scheduling platforms, pharmacies, or some other type of third-party server. The smart animal devices of the platform, such as the smart food and smart water dispensers, may each have a VPN or other connection type to the platform 101 for improved security of communications. A plurality of platform 101 databases and data facilities may be included within and/or associated with the platform 101. Such platform data may include, but is not limited to, animal data, event data, smart device data, historical data, population data, guideline data, or some other type of data. The platform 101 may include a data integration system for integrating data across smart animal devices, as well as external data sources.

In embodiments, animal data may include, but is not limited to, information pertaining to an animal in proximity to a smart animal device, such as animal name, animal type, breed, birthdate, weight, or some other type of data related to an animal. Animal data may include animal health data, such as veterinary records. Event data 116 may include, but is not limited to, information related to animals in proximity to or in interactions with smart animal devices, such as the number and timing of feedings at an animal food dispenser, the duration of time an animal laid on an animal bed, the timing of an animal entering or exiting an animal door, or some other type of event data. Smart animal device data may include, but is not limited to, characteristics or actions associated with a smart animal device, such as device type, model, identifying number, dates in service, dates of maintenance events, usage events, or some other type of smart animal device data. Historical data may include, but is not limited to, longitudinal data related to animal activities, such as historical time series data on animal feeding history, sleep history as indicated by longitudinal data from an animal bed, activity amounts for a prescribed time period, such as a weekly activity history, or some other type of historical data. Population data may include, but is not limited to, grouped animal data of relevance to a target animal that is monitored by the platform 101, for example data indicating the typical feeding timing and amounts for a population of animals matched to the target animal by age, breed, size, or some other criterion. Guideline data may include, but is not limited to, data summarizing recommendations for animal care, such as feeding or animal weight maintenance goals, recommended activity level(s), or some other guideline that may be used to measure, monitor and schedule platform 101 activity in accordance with a guideline or recommendation (e.g., a veterinarian's recommendation regarding an animal's feeding schedule).

In embodiments, the platform 101 may include an analytics engine. The analytics engine may include, but is not limited to, a learning machine, a prediction module, a personalization module, an automation module, or some other type of analytic processing module. The analytics engine may intake data that is collected by the platform 101, for example, data relating to the usage of smart animal devices, or data that is obtained by external data sources that derive from outside the platform 101. The analytics engine may build, test and validate machine learning algorithms and models based at least in part on ingested and/or data collected within or by the platform 101 and use such algorithms and models for the purposes of predicting, automating and/or personalizing the performance of the platform 101 and its utilization of smart animal devices 101. The analytics engine may perform platform data processing on platform data and/or data from external data sources. For example, processing may be used to optimize the placement of smart animal devices to encourage wanted animal behaviors. Outcomes and actions taken, based at least in part on such processing, may be automated by the analytic engine of the platform 101.

In embodiments, the platform 101 and the smart animal devices associated with the platform may be located outdoors or indoors, for example, at or within a home, barn, or other facility type, such as a veterinary facility or business, that includes other smart devices that may be operatively connected with the platform, such as an alarm or security system, surveillance camera, webcam, sound system or microphone, including a smart personal assistant device, each of which may be further operably connected with a third party platform or service including, but not limited to, a social media platform. The platform 101 may be further associated with other devices, such as wearable devices, mobile computing devices, or some other device type, and such devices may receive real time reporting and/or summary reports and alerts regarding animal behaviors and/or smart animal device data. In embodiments, alerts may be sent by text, email, phone call, social media post, direct messaging, or come other communication means.

In embodiments, external data sources may include, but are not limited to, third party animal data, veterinary clinical data, lab data, pharmacy data, vaccine data, scheduling data, financial data, educational content, after-care, dosage and procedure reference libraries, third party data, advertising content, or some other type of external data. A third-party server or plurality of third-party servers may also be operatively connected with the platform 101.

In embodiments, the platform 101 may provide an application programming interface (API) and a software development kit (SDK) to enable developers and development platforms to create applications to interact with the platform. An application and graphical user interface (GUI) may be associated with the platform 101 and used to configure, operate and/or visualize aspects of the platform's performance. The GUI may include a set of interfaces and services for user configuration of smart animal device usage, such as the timing of an animal's feeding, the duration of the feeding, and the amount of food to be dispensed during the feeding. The GUI may be viewed on a computing device including, but not limited to, a mobile computing device or web browser. The platform 101 may include a set of end user mobile application interfaces configured in the platform for allowing a platform user to configure a set of parameters of the platform 101.

In embodiments, the platform 101 may include a plurality of outbound data functions including reporting, such as reporting to a computing device, veterinary clinic, social media, third party platform, and/or general communications platforms such as email.

In an example embodiment of the present invention, a user may open the platform application that is operably connected to the platform 101 and, within the GUI, view the smart animal devices that are connected to the platform. In this example, the smart devices include an animal food dispenser, animal bed, and animal door. Using the platform application, the user may be able to select a smart animal device for configuration. Configuration may be a set up step for an initial usage of a smart animal device or it may be to adjust the usage of a smart animal device that is already in operation. For example, following a dog's check-up visit with a veterinarian, a user may configure an animal food dispenser to present a set amount of food, and a timing of feedings, that is in accordance with the veterinarian's recommendation. Alternatively, external data related to the amount and timing of feedings may be provided to the platform 101 and used by the analytic engine to model and automate the appropriate amount and timing for the food dispenser to present feedings to the dog. The dog may have a wearable device, such as a smart collar that includes an RFID or other means of storing and communicating data regarding the dog, such as animal name or another, possibly unique, identifier. The platform may detect the presence of the dog and command the animal food dispenser to select a food type and/or amount and present the dog for feeding at a set time, or plurality of times, all in accordance with a personalized feeding amount/schedule that is stored by the platform. The animal food dispenser may record data about the feedings, such as the weight of the amount of food initially presented to the dog for feeding and the weight of the total amount consumed by the dog. The food may be made available to the dog until it is completely consumed (e.g., as detected by weight), or alternatively the food may be presented for only a specified time duration and the food receptacle retracted back into the body of the food dispenser upon completion of the time duration, regardless of the amount consumed. Continuing the example, a smart animal bed and smart animal door may be connected to the platform and record the number and timing of the dog's entry and exit from a home, and the timing and duration that the dog was on the smart animal bed, including how active the dog was on the bed (e.g., motionless, indicating the dog was sleeping). The platform may use data from one smart animal device to determine the usage of a second smart animal device. For example, the platform may store a correlation between an activity level criterion and a feed amount, whereby, the activity recorded by the smart animal bed and smart animal door are used to measure an activity level for the dog over a specified time period, compare it to the stored activity level criterion, and use this data to determine an appropriate amount and/or timing of feeding to provide the dog. A more active dog, as indicated by less time spent on the smart animal bed and/or a greater amount of entry/exits as recorded by the smart animal door, may be provided a larger amount of food by the smart animal food dispenser relative to a less active dog. As the platform records the activities of the animal, a user may be provided real time updates to the platform application or some other reporting platform, as described herein. Alternatively, the data recorded by the platform 101 regarding the activities of the animal may be provided in a summary format according to a schedule set by the user. Reporting may include sending alerts, emails, phone calls or other communications according to rules set by the user. For example, extended inactivity of the animal, as measured by a long period of the animal lying on the bed motionless, may trigger the platform sending a text alert to a mobile computing facility that is associated with the user, or some other party. The alert may note for the user that the dog has been inactive and may include a link to other of the smart devices associated with the system, such as a camera with which the user may view the dog to gauge its condition, or a microphone and speaker through which the user may call or signal the dog to determine that the animal is not experiencing a health event. Similarly, the platform may detect, record and alert a user when an animal is detected exiting a home at the smart animal door, but has not reentered the home for a specified duration. Rules may be associated with sending alerts, for example external data related to weather such as precipitation and temperature may be used by the platform to detect an event for which a user should be alerted. For example, a rule may state that when the temperature is between 60 and 90 degrees Fahrenheit, an alert will not be sent regarding a time period following an animal exiting and not returning through the smart animal door, however if the temperature is greater than 90 degrees an alert will be sent if the animal door does not detect the animal's reentry within a predetermined amount of time, e.g., 45 minutes. Such external environmental data may also be used by the platform to determine a watering schedule for the animal. An animal that is not consuming a specified amount of water, given a particular environmental condition (e.g., a very hot day), may generate additional alerts to a user. In embodiments, and alert may be an email, text, phone call, social media post, direct message (including, but not limited to a direct message on a third-party platform such as a social media platform), or some other communication means. Alerts may be generated by a neural net, or some other artificial intelligence, machine learning, or other computational technique, that is trained to recognize patterns, including behavioral patterns, and detect anomalies, outliers, low probability events, events that match a specified criterion, or some other trend or event of interest. Such detection of anomalies, outliers, low probability events, events that match a specified criterion, or some other trend or event may be analyzed in conjunction with external data and/or other data collected by the platform 101 including, but not limited to, weather, time of day, prior history of an animal's or group of animals' behavior, or some other datum or data).

Figure 13:
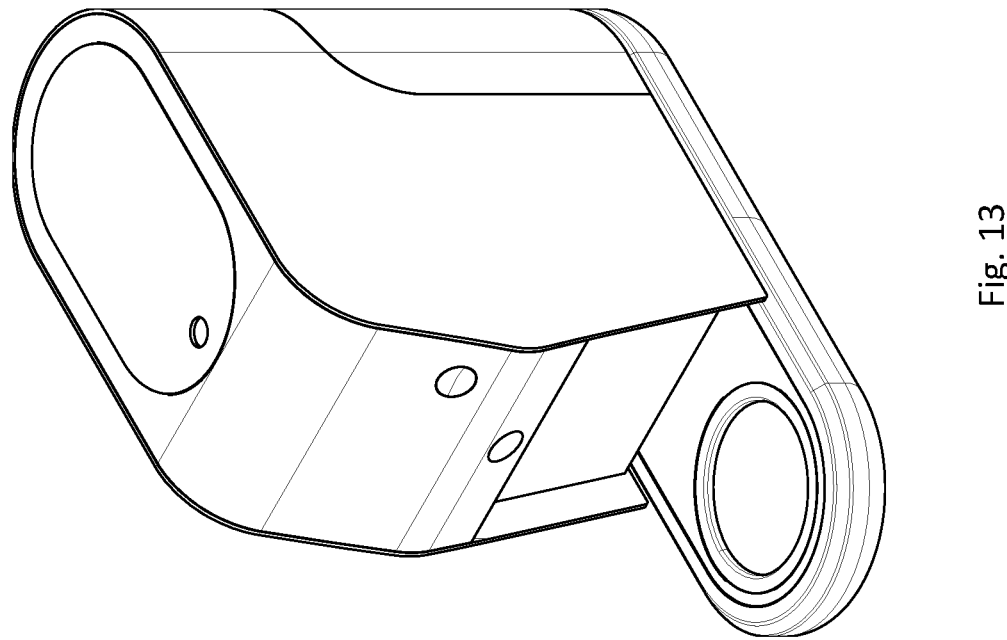
FIG. 13 is a perspective view of a smart animal food dispenser.

Referring to FIG. 13, a smart animal food dispenser is shown. The smart animal food dispenser may include a plurality of interior compartments in which animal food, animal treats, animal medication, or some other animal consumable may be stored. Prior to discharge from the smart food dispenser into a receptacle to present to an animal for feeding, a plurality of food products, or wet and dried goods, may be blended from independent compartments of the smart food dispenser. For example, one compartment may contain food and a second compartment may contain medicine, one compartment may contain dry food and a second compartment may contain wet food, etc. Prior to dispensing, a specified amount of medicine may be added to the food to provide to an animal. The mixing of the medicine and food may take place within a mixing compartment of the smart food dispenser. Alternatively, the mixing of the medicine and food may take place within the receiving receptacle (e.g., the bowl from which an animal will consume the mixture). In an alternate embodiment, the smart food dispenser may include interior compartments for separately storing wet and dry ingredients to be combined prior to consumption by an animal. For example, one interior compartment may contain wet food in packaging and a second compartment may contain dried vitamin supplements to be added at a specified amount prior to consumption by an animal. Animal food may include dry animal food, wet animal food, some combination of dry and wet food, room temperature animal food, or animal food that is heated or cooled to a desired temperature. Animal food may be stored in a containerized, packaged form, or in a loose, bulk form. In an example, wet animal food may be sterilized and packaged in premade, sealed containers that may be stacked within the smart food dispenser and/or inserted into a receiving slot of similar facility of the smart food dispenser.

Figure 14:
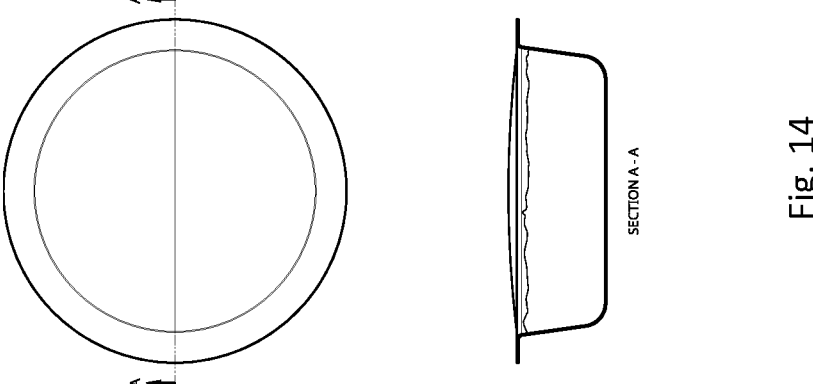
FIG. 14 illustrates animal food packaging for use in a smart animal food dispenser in accordance with the present disclosure.

Similarly, dry food also may be packaged in such premade-sealed containers. FIG. 14 shows an example of smart animal food packaging in a containerized (e.g., pod) form suitable for loading for distribution using a smart animal food dispenser, as described herein. The packages may be sealed, for example, using a metalizing or other sealing film, cover, or the like. In embodiments, the packaged food may contain a food amount that is set to a specific calorie count, nutritional balance or some other criterion. The food type and food amount may be specifically tailored to an animal size, animal breed, animal age, animal health prescription, animal weight, animal measurement, or some other criterion including even to a specific animal (e.g., recipes customized for the specific nutritional or dietetic needs of the animal such as for losing weight, gaining weight, controlling diabetes, etc.). The packages may include grooves, ridges, or other features such as to help control the rate at which the animal consumes the food. A package of food (or multiple packages of food) may be selected by the smart food dispenser or otherwise dispensed for presenting to an animal for feeding and, as part of the movement of the packaged food to an exterior location to permit feeding, the packaged food may pass across, through, or under an unsealing mechanism in order to expose the food for consumption by the animal or animals. In an example, the unsealing mechanism may be a flange, slicer, knife, pincer, peeler, or some other element capable of insertion between a vessel containing a food product and a seal, film or other covering that adheres to the vessel to protect the food from spoilage. In another example, the smart food dispenser may have a unit, arm, probe, extension or other apparatus outfitted with an adhesive that, when pressed against the seal, film or other covering that adheres to the vessel to protect the food from spoilage, allows the unit, arm, probe, extension or other apparatus outfitted with an adhesive to pull the seal, film or other covering from the vessel, exposing the consumable within the vessel. In embodiments, the unsealing mechanism may peel the package seal back from the vessel, exposing the food product. The smart food dispenser may include a scanner or other mechanism for monitoring food packages prior to dispensing and/or at the time of dispensing, e.g., for monitoring the food being consumed by the animal and for planning meals for the animal (e.g., different packages may have different nutritional or caloric details that can be used to decide whether and when to dispense another food package). Used food packages may be retracted back into the smart food dispenser. In an example, the unsealing mechanism may leave a portion of the seal in adherence to the vessel so that once the feeding ends the smart food dispenser may retract the vessel package, with the seal still partially attached, back into the smart food dispenser in order to store the used package within an interior compartment of the smart food dispenser that is designed to hold used food packaging. In this way, the smart food dispenser may create no trash, discards or other packaging elements that remain outside of the smart food dispenser. This may prevent an animal from returning to eat food products that have been exposed long enough to develop contamination or some other unwanted byproduct, such as foul odor or insect attractant. In another example, the food packaging may include a tab on a seal of the packaging, allowing for the smart food dispenser to grasp the tab and peel back the seal in order to expose the food for consumption by an animal.

In embodiments, animal food stored in the smart animal food dispenser may be gravity fed into a receiving receptacle when the receiving receptacle is retracted into the body of the smart animal food dispenser, underneath the food storage compartment. Alternatively, food may be mechanically moved from the food storage compartment into the receiving receptacle. The food storage compartment and/or receiving receptacle may measure the amount of food or other consumable by volume, by weight, by height, by number of packaged units, by visual inspection using a camera, or some other measurement. Such detection at the receiving receptacle from which the animal consumes the food may allow the smart food dispenser, and platform 101, to continuously measure the amount of material consumed, the rate at which it was consumed, the intervals at which it was consumed (e.g., half, for example by weight, consumed in 60 seconds, followed by no consumption for two minutes, followed by consumption of the second half over 90 seconds), the amount not consumed, or some other measure of the consumable in the receiving receptacle. The smart food dispenser may include a unit counter and the platform 101 may monitor the units, weight or some other measure associated with the amount of food within a smart food dispenser and automatically order additional food for the dispenser from a supplier once the smart food dispenser communicates reaching a specified threshold of food amount at which an order should be generated. Additionally or alternatively, the smart food dispenser may generate one or more notifications upon reaching a specific threshold of food amount (e.g., on the smart food dispenser itself and/or to the system). Customer data, such as address and billing information, may also be stored by the platform 101 in order to place the order. Placement of an order may generate an alert to a party associated with an account to which the smart food dispenser is assigned. Additional parties may also be listed within a platform 101 account to receive alerts regarding the feeding and behaviors of an animal or plurality of animals, such as house sitters, animal sitters, dog walkers, vets, or some other interested party.

In embodiments, the smart animal food dispenser may detect, read and process data, including data from smart animal wearables like a smart animal collar outfitted with an RFID or some other means of identification, in order to accurately identify an animal and, using the platform's data and analytic engine, determine an appropriate feeding amount and timing for feedings. As the smart animal food dispenser initiates an animal feeding, it may communicate this to the platform and continue to record data related to the feeding while the animal feeds, including the amount and rate of the feeding, the duration of the feeding, or some other feeding characteristic. This data may be sent by the platform, in real time and/or in summary form, to a user, such as the animal's owner. The smart animal collar, for example with RFID, may also detect the presence of more than one animal at the smart food dispenser and delay or otherwise alter the presentation of food to the animal that is intended to feed until the smart food dispenser detects that the animal that is not scheduled to feed has withdrawn from the proximity of the smart food dispenser. This may allow the smart food dispenser to prevent or minimize the risk of a dominant animal consuming food that is intended instead for a less dominant animal. The smart animal food dispenser may include WiFi and/or other appropriate communication capabilities (e.g., Bluetooth, near-field communications, etc.), heating and cooling units, a camera, a microphone, a motion detector, and/or some other sensor type. A back portion of the smart food dispenser may include a transparent element that allows a user to see into the food storage compartment to determine the amount of food the smart food dispenser currently stores. Alternatively, the measure of available food may be automated by the smart food dispenser, as described herein. The smart food dispenser may include an upper lid element, including a locking facility, that allows a user to secure the food storage compartment. "Food" as used herein should be understood to include wet and dry consumable products including, but not limited to, wet food, dry food, mixed wet and dry food, animal treats, livestock supplements, animal byproducts (e.g., bones, pigs ears, and the like), attractants (e.g., cat nip), or some other animal product.

Referring to FIG. 15, a smart animal water dispenser is shown. The smart water dispenser may include a plurality of interior compartments in which water, animal medication, or some other liquid animal consumable may be stored. Prior to discharge from the smart water dispenser into a receptacle to present to an animal for watering, a plurality of liquids, or liquid and dried goods, may be blended from independent compartments of the smart water dispenser. For example, one compartment may contain water and a second compartment may contain medicine in liquid form. Prior to dispensing, a specified amount of medicine may be added to the water to provide to an animal. The mixing of the medicine and water may take place within a mixing compartment of the smart water dispenser. Alternatively, the mixing of the medicine and water may take place within the receiving receptacle (e.g., the bowl from which an animal will consume the liquid mixture). In an alternate embodiment, the smart water dispenser may include interior compartments for separately storing wet and dry ingredients to be combined prior to consumption by an animal. For example, one interior compartment may contain fresh water and a second compartment may contain dried vitamin supplements to be added at a specified amount prior to consumption by an animal. Water or other liquid animal consumable may be held within the smart water dispenser at room temperature, or it may be heated or cooled to a desired temperature. A heating unit may serve as a defrosting unit in use cases where the smart water dispenser is placed in an environment with sub-freezing temperatures, such as outdoors for use with livestock. In an example, the smart water dispenser may have a shroud, insulation, or some other protective layer to reduce internal temperature fluctuations. Water stored in the smart water dispenser may be gravity fed into a receiving receptacle when the receiving receptacle is retracted into the body of the smart water dispenser, underneath the water storage compartment. Alternatively, water or liquid may be physically moved (e.g., pumped) from the water storage compartment into the receiving receptacle. In embodiments, the smart water dispenser may be attached to, connected to, plumbed with, and/or have some other type of connection to a fixed water source. A fixed water source may include, but is not limited to, household interior plumbing (e.g., faucet, wall water outlet, and the like), exterior plumbing (e.g., hose spigot, stand pipe, pump, sprinkler system, irrigation system, and the like), or some other type of fixed and/or automatically replenishable water source.

In embodiments, the smart water dispenser may include a filtration module that filters liquid prior to presenting it to the receiving receptacle for consumption by an animal. In an example where the smart water dispenser is mixing water with another substance, such as medicine, the filtration system may only filter the water prior to mixing the medicine, rather than mixing the combination of the water and medicine, in order to preserve the integrity of the compounds within the medicine, or other substance to be combined with the filtered water. The water storage compartment and/or receiving receptacle may measure the amount of water or other liquid by volume, by weight, by height, or some other measurement. The smart water dispenser may estimate the amount of water or other liquid that is lost due to spillage, splashing and the like. This estimation of loss may be based at least in part on audio, audio/visual and/or weight data collected by the smart water dispenser as an animal consumes the liquid.

In embodiments, the smart water dispenser may detect, read and process data, including data from smart animal wearables like a smart animal collar outfitted with an RFID or some other means of identification, in order to accurately identify an animal and, using the platform's data and analytic engine, determine an appropriate watering amount and timing. As the smart water dispenser initiates an animal watering, it may communicate this to the platform and continue to record data related to the watering while the animal drinks, including the amount and rate of the watering, the duration of the watering, or some other watering characteristic. This data may be sent by the platform, in real time and/or in summary form, to a user, such as the animal's owner. The smart water dispenser may include WiFi capabilities and/or other appropriate communication capabilities (e.g., Bluetooth, near-field communications, etc.), heating and cooling units, a camera, a microphone, a motion detector, or some other sensor type. A back portion of the smart water dispenser may include a transparent element that allows a user to see into the water storage compartment to determine the amount of liquid the smart food dispenser currently stores. Alternatively, the measure of available water or liquid may be automated by the smart water dispenser, as described herein. The smart water dispenser may include an upper lid element, including a locking facility, that allows a user to secure the water storage compartment and prevent spillage.

In embodiments, the smart animal food dispenser and the smart water dispenser may be used independently of the other or as a paired feeding and watering station. Alternatively, components of the smart animal food dispenser and the smart water dispenser may be incorporated into a single unit, in which case the smart animal food dispenser and the smart water dispenser may be controlled separately and/or in a coordinated manner. Such apparatus can be configured to allow water to be added to dry animal food within the apparatus or within a receptacle to present to an animal for feeding and/or drinking.

Figure 2:
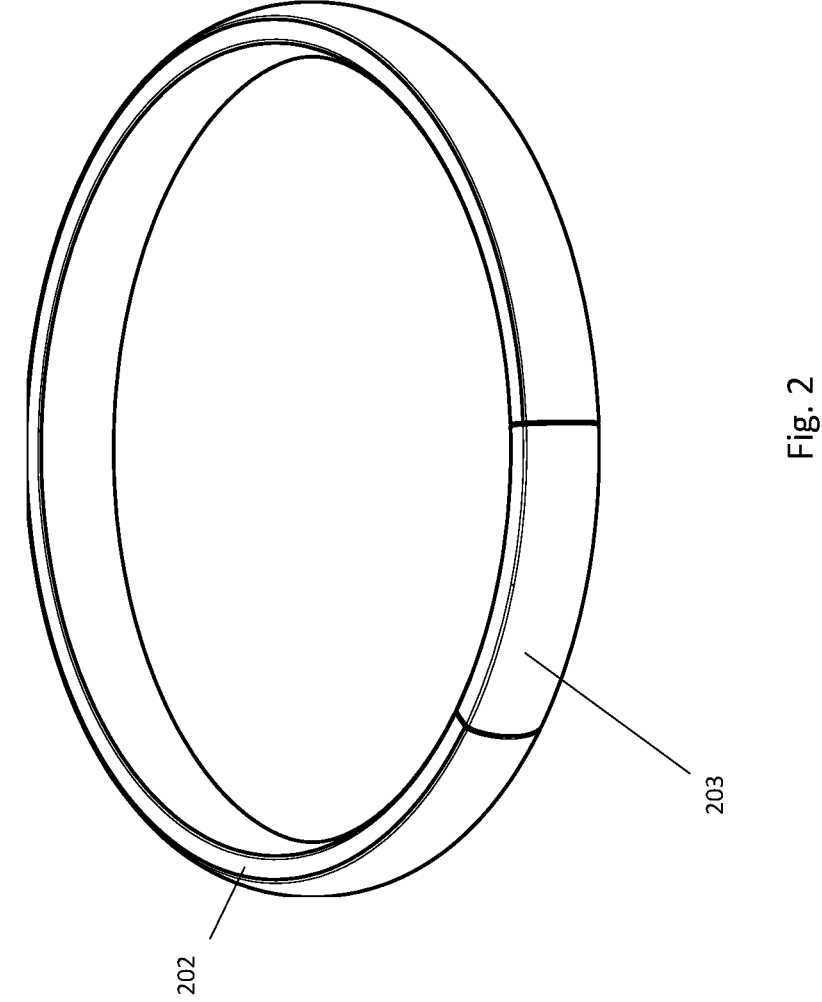
FIG. 2 illustrates a smart animal collar in accordance with the present disclosure.

Referring to FIG. 2, a smart animal collar is shown. As described herein, the smart animal collar may include identifiers, including but not limited to an RFID tag, that may be read by the smart animal devices and/or platform 101. In embodiments, a smart animal collar may have an appendage, pendant, extension or other component, such a component may contain an RFID tag, microchip, or other component capable of storing data related to an animal and transmitting to or otherwise communicating with the platform 101. The smart collar might consist of two parts, the band 202, and the housing 203. The housing might contain an energy harvesting device to provide power for activity and/or location tracking.

Figure 3:
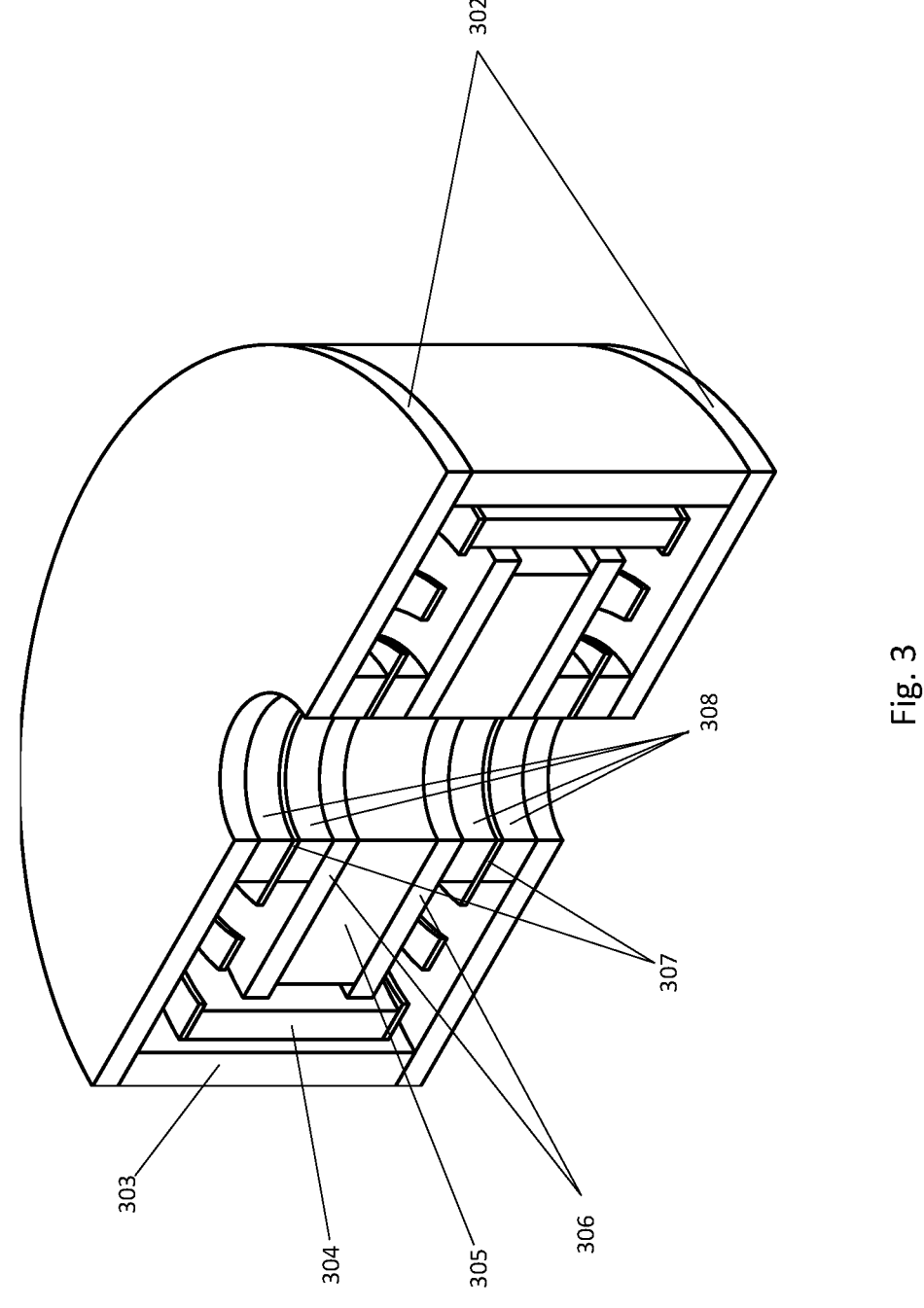
FIG. 3 illustrates a device for harvesting energy from locomotion.
Figure 4:
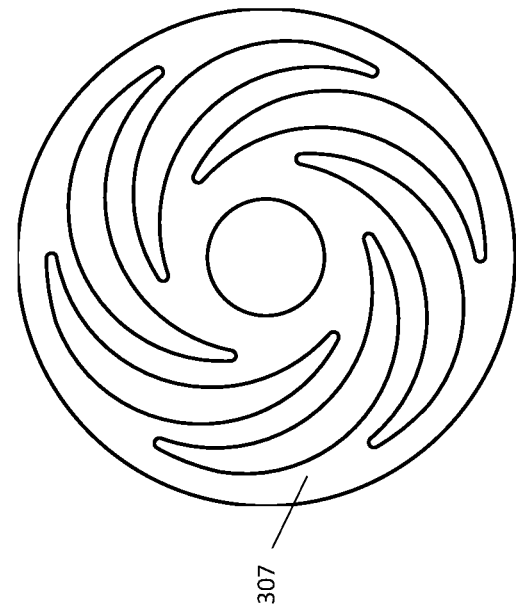
FIG. 4 illustrates a flexural spring which is an integral part of the energy harvesting device.

Referring to FIGS. 3 and 4, an energy harvesting device 301 could be used to extract electrical energy from the natural frequency of an animal gait. This device might consist of a self-supporting center-tapped coil 304 suspended by a pair of flexural springs 307. This coil 304 would be constrained to oscillate along a nearly-linear path. As the coil oscillates, magnetic flux from a magnet 305 would be concentrated through the coil by ferromagnetic pole pieces 306 and ferromagnetic outer ring 303. The relative arrangement of these components can be ensured, for example, by paramagnetic support plates 302, support spacers 308 and suitable adhesives. A hole through the whole of the energy harvesting device would allow for attachment or mounting. The stiffness of the flexures 307 and the mass of the coil 304 would set the undamped natural frequency of oscillation. The addition of an electrical load would tend to broaden the resonant frequency. This damped natural frequency could be matched to the natural stride frequency of the animal to optimize energy harvesting.

Figure 5:
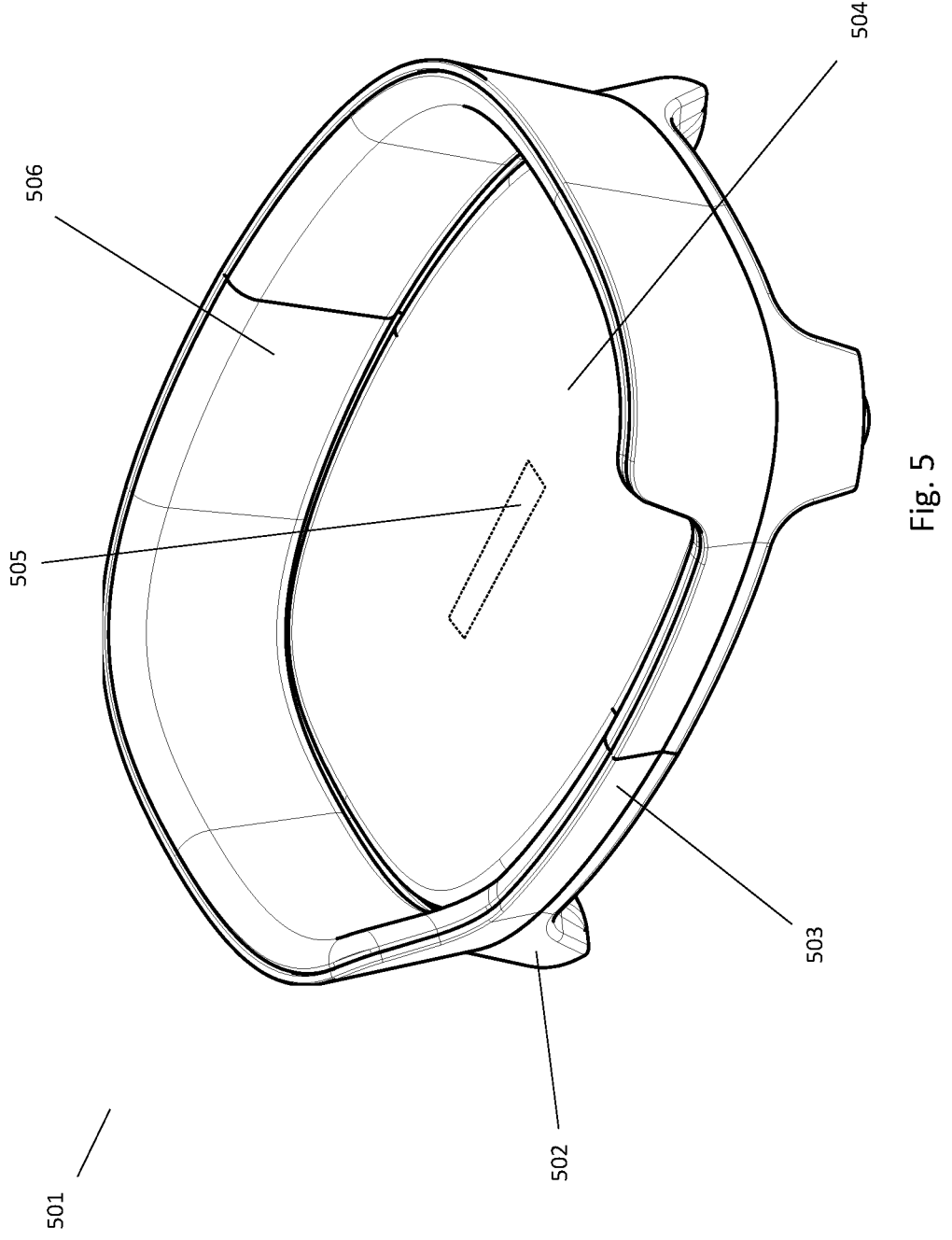
FIG. 5 is a pictorial view of a smart pet bed with provision for vital statistics monitoring and temperature control.

A smart animal bed 501 having a temperature control unit and sensors is shown in FIG. 5. This bed 501 consists of a base 502, an arrangement of walls 503 to which padding is affixed 506, a thermally conductive gel-padded surface 504, into which a film-type piezoelectric sensor 505 is integrated.

Figure 6:
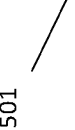
FIG. 6 is a plan and section view of a smart animal bed in accordance with the present disclosure.
Figure 7:
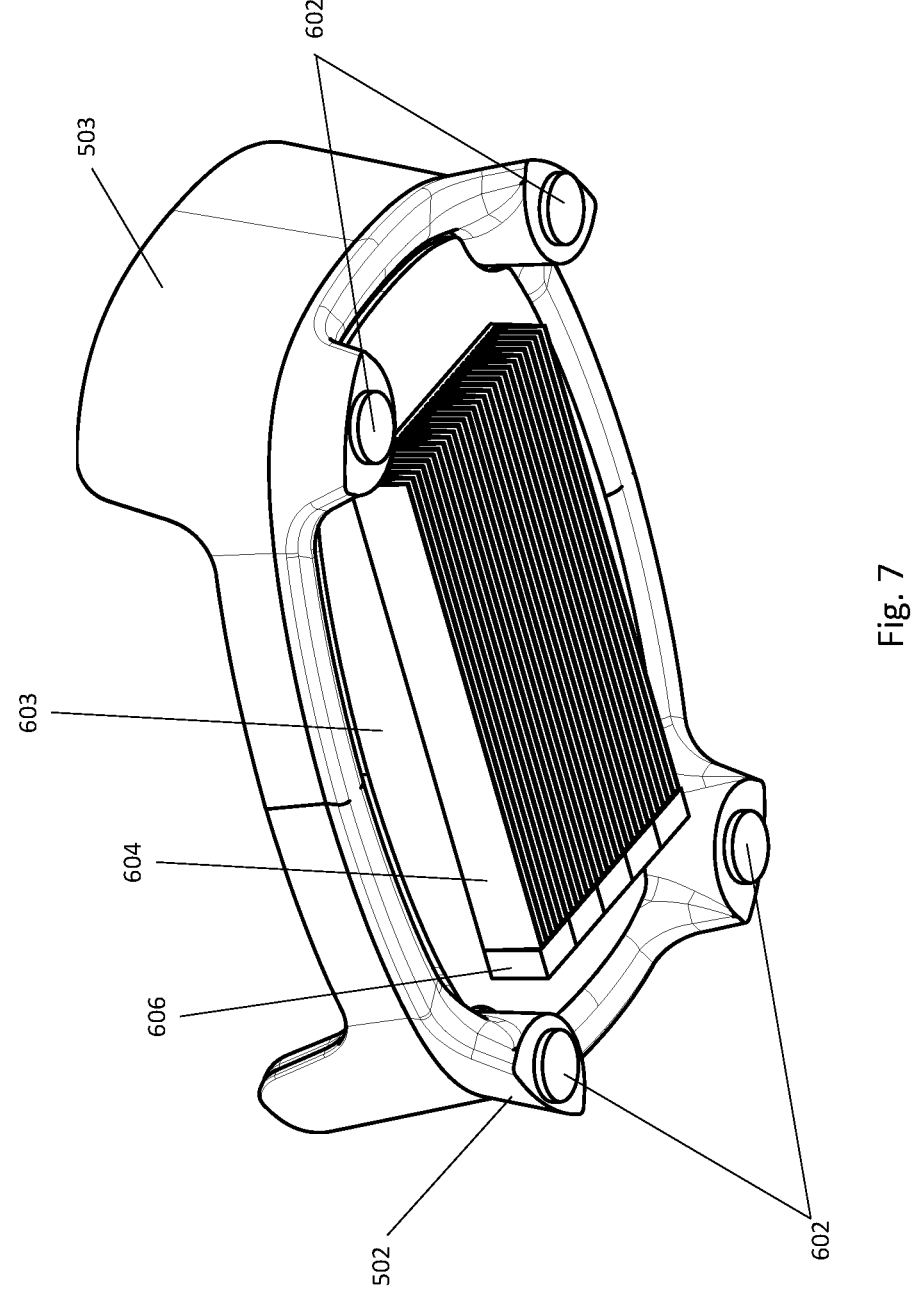
FIG. 7 is a pictorial view of the bottom of the smart pet bed showing disposition of component parts.

As seen in FIGS. 6 and 7, this smart animal bed 501 can provide or remove heat from the sleeping surface 504. Heat is removed from the sleeping surface through a thermally conductive gel pad 504 which is affixed to a thermally conductive baseplate 601 made of aluminum, copper or other thermally-conductive material. The thermal connection between the gel pad 504 and the baseplate 601 is assured through the use of a suitable adhesive (not shown). The baseplate is covered, from beneath, with a thermal insulator 603 such as neoprene foam rubber or expanded polystyrene foam. This insulator ensures that heat removed from the gel pad 504 is not re-introduced to the baseplate 601 from the heat sink 604. Heat is pulled from the baseplate 601 by one or more thermoelectric heat pump devices (e.g., Peltier devices) collectively numbered 605. Each of these thermoelectric devices 604 is in low-thermal-resistance contact with the base plate 601 and the heat sink 604. Heat pulled through these devices 605 is then offloaded to the environment by a heat sink 604 and a plurality of fans 606. The heat sink 604 has a set of debossed pads designed to contact the Peltier devices, while allowing a reasonable thickness for the insulation 603. Owing to the symmetric nature of the Peltier effect, providing heat to the gel pad is accomplished simply by reversing current flow through the Peltier thermoelectric devices 605. Power to the Peltier devices is provided by an external power source (not shown).

In order to assess the wellbeing of the animal, the sensor 505 provides a fluctuating charge in response to movement-induced flexing via the piezoelectric effect. This fluctuation can be processed to extract such things as respiration and heart rate information, restlessness (e.g., sleep problems and nightmares), nervousness (e.g., shivering/shaking during a thunderstorm), etc. Further, a plurality load cells 602 are positioned between the base 502 and the surface upon which it rests. These load cells 602 experience a change in resistance with strain. As per standard practice, a Wheatstone bridge converts these changes in resistance to voltage signals that are analyzed to assess weight of the animal any time the bed is in use. The weight and other information can be used by the platform 101 to assist in determining overall health and establishing patterns of behavior.

Figure 8:
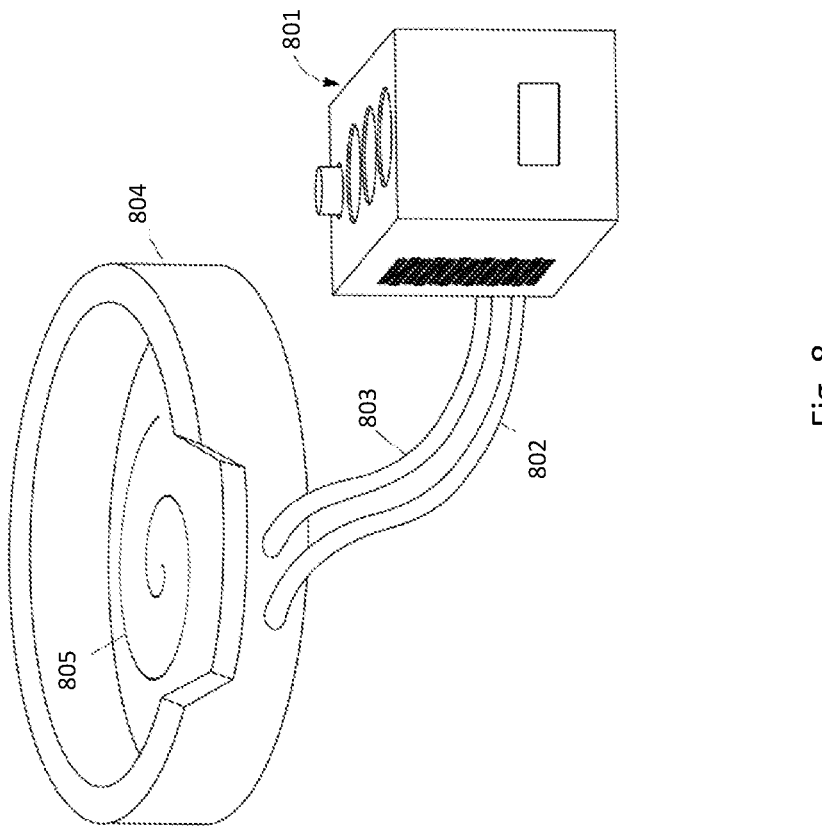
FIG. 8 is an environmental perspective view of an alternate temperature-regulated animal bed having a surface temperature zone connected to a temperature control unit according to an exemplary embodiment of the present disclosure.
Figure 9:
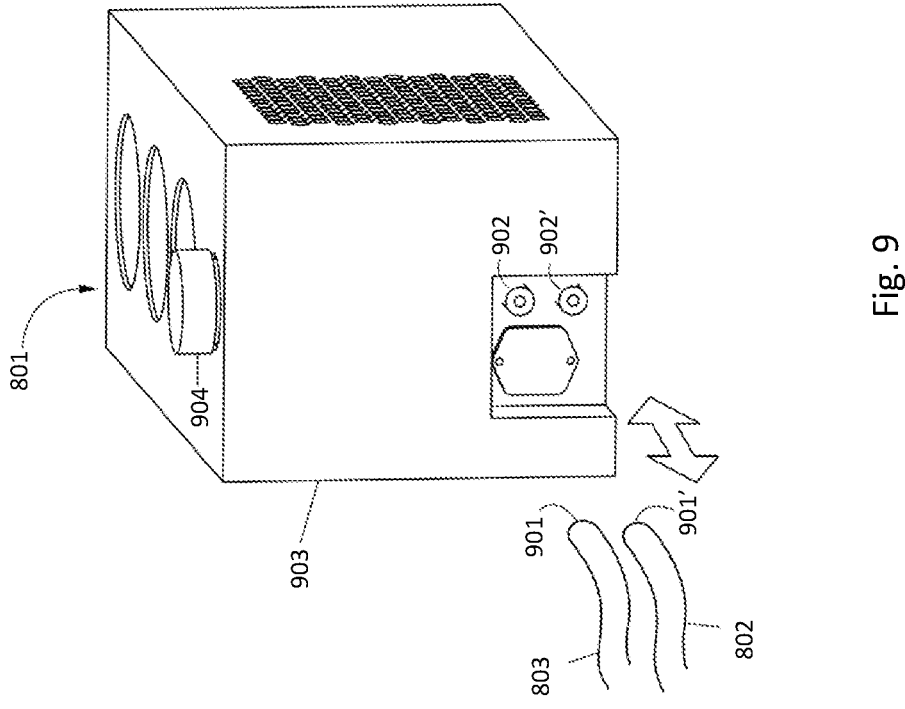
FIG. 9 is a perspective view of the exemplary control unit demonstrating the quick connection/disconnection of the flexible water supply and return lines.
Figure 10:
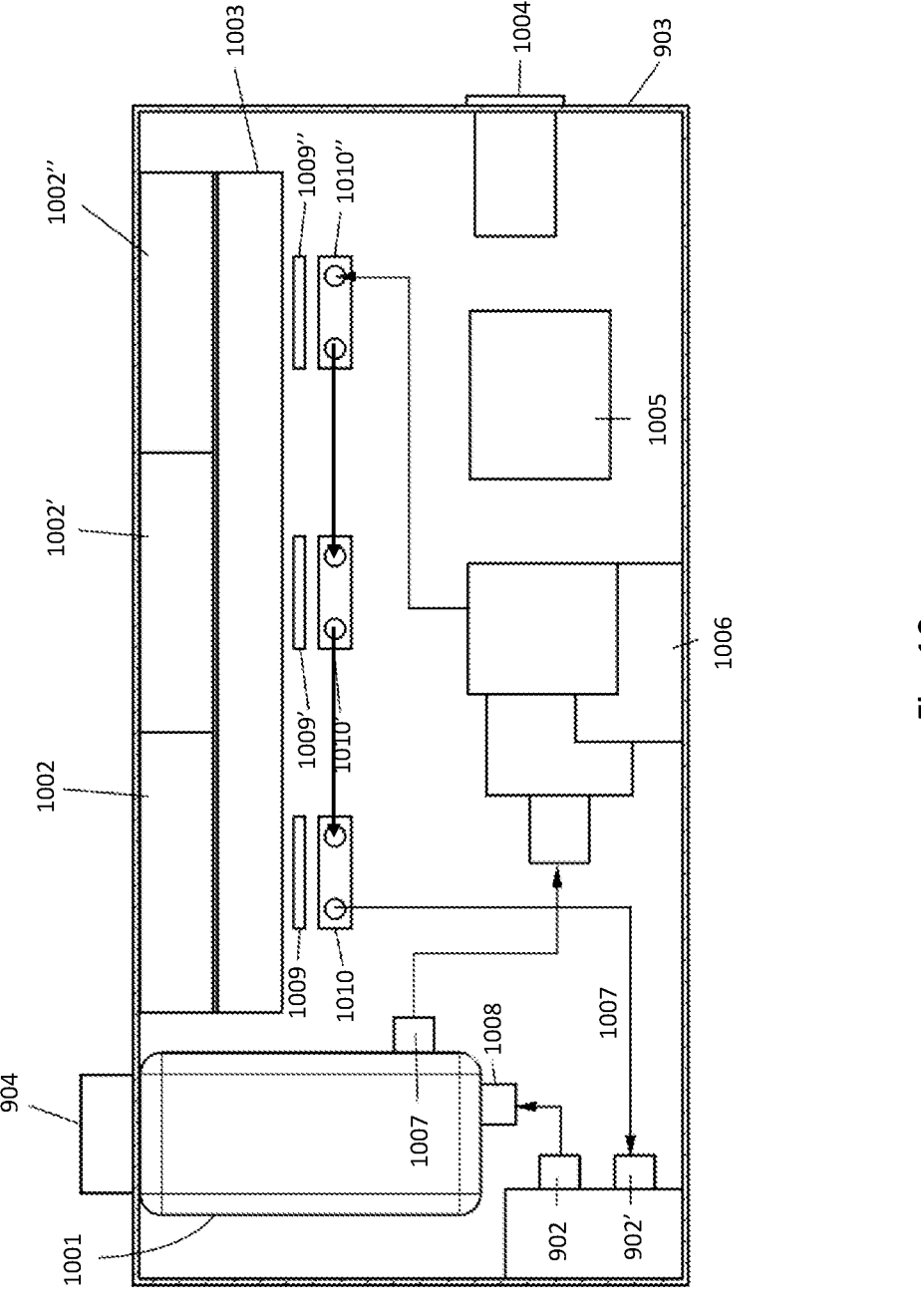
FIG. 10 is a side schematic view showing various internal components of the exemplary control unit fluidly connected to the animal bed.

Another smart animal bed having a temperature control unit according to one exemplary embodiment of the present disclosure is illustrated in FIG. 8. The temperature control unit may adjust the smart animal bed temperature based at least in part on animal's temperature and/or an external environment temperature (e.g., indoor temperature of a household, ambient temperature of a barn, outdoor temperature in proximity to an animal, and the like). In the exemplary implementation shown, the control unit 801 is attached through flexible conduit to a temperature-conditioned article, such as animal bed cushion 804. The animal bed cushion 804 may have a thermally regulated surface zone comprising internal flexible (e.g., silicon) tubing 805 designed for circulating heated or cooled liquid within a hydraulic circuit between the control unit 801 and animal bed cushion 805. As shown in FIGS. 9 and 10, the flexible conduit assembly for each control unit 801 comprises separate liquid supply and return lines 802, 803 fluidly connected to tubing 805, and quick-release female connectors 901, 901' for ready attachment and detachment to external male connectors 901, 902' of the control unit 801. In alternative exemplary embodiments, the temperature control unit 801 may be operatively connected (e.g., by flexible conduit) to any other temperature regulated article, such as a blanket or other bedding or covers, seat pad, sofa, chair, mattress, or the like.

As illustrated schematically FIGS. 9 and 10, the exemplary control unit 801 comprises an external rectangular prism-shaped housing 903, and a liquid reservoir 1001 located inside the housing 903. The reservoir 1001 has a fill opening 904 accessible through a removably capped opening 904 (FIG. 10) in housing 801, a liquid outlet 1007, and a liquid return 1008. Liquid contained in the reservoir 1001 may be moved in a circuit through a conduit assembly comprising in-housing tubes 1007, the flexible supply and return lines 802, 803, and flexible silicone tubing 805 within the temperature-regulated pad 804. The liquid may be selectively cooled, as described herein, by cooperating first and second heat exchangers 1101, 1103 and thermoelectric cooling modules 1009, 1009', 1009". The cooling modules 1010, 1010', 1010" may reside at an electrified junction between the first and second heat exchangers 1101, 1103, and function to regulate liquid temperature from a cool point of as low 71 degrees F., or cooler. The housing 903 and reservoir 1001 may be either separately or integrally constructed of any suitable material, such as an anti-flammable ABS, polypropylene, other molded polymer, or aluminum.

Figure 11:
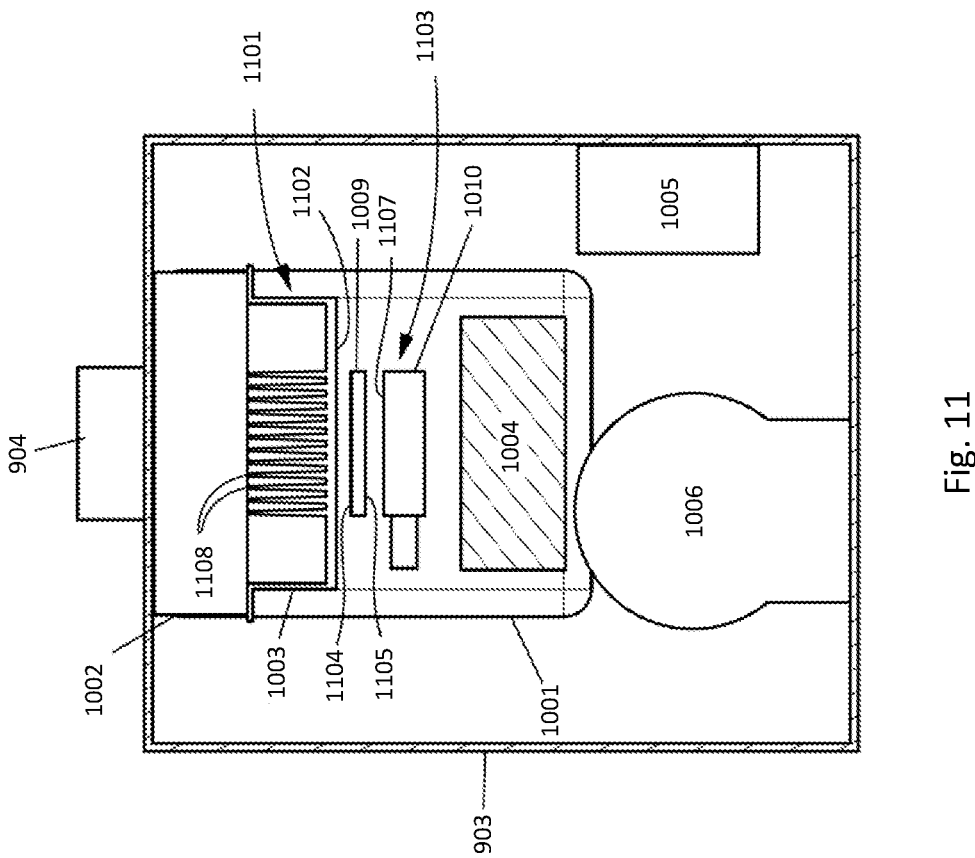
FIG. 11 is a front schematic view of the exemplary control unit.
Figure 12:
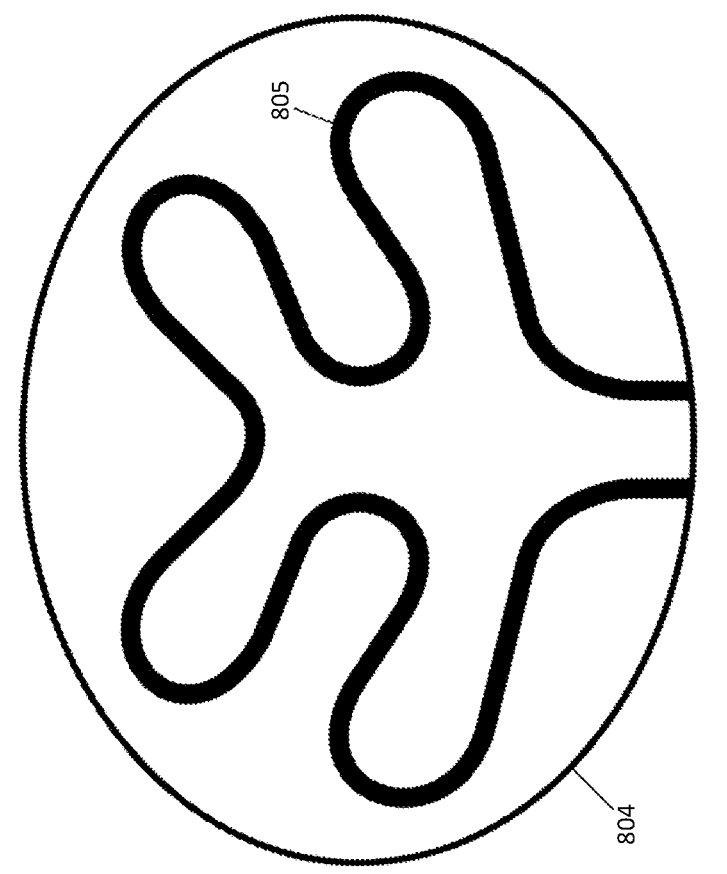
FIG. 12 provides a simplified illustration of a path for temperature transfer tubing in a cushion of an animal bed for circulating heated or cooled liquid in accordance with an embodiment.

Referring to FIGS. 9, 10 and 11, the first heat exchanger 1103 comprises liquid heat exchanger blocks 1010, 1010', 1010" communicating with in-housing tubes 1007, and cooperating with thermoelectric cooling modules 1009, 1009', 1009" to heat or cool the liquid inside the in-housing tubes 1007 to a selected (set) temperature. Each liquid heat exchanger block 1010, 1010', 1010" has a substantially planar metal base 1107, and at least one passage for flow of a heat transfer liquid therethrough. The exemplary cooling modules 1009, 1009', 1009" are operatively connected to an internal power supply 1005 and main control board 1004 and comprise respective thin Peltier chips having opposing planar upper and lower major surfaces 1104, 1105. The lower major surface 1105 of each cooling module 1009, 1009', 1009" resides in direct thermal contact with the planar base 1107 of its corresponding liquid heat exchanger block 1010, 1010', 1010". A thermal pad or compound (not shown) may also reside between each cooling module 1009, 1009', 1009" and liquid heat exchanger blocks 1010, 1010', 1010" to promote thermal conduction from lower major surface 1105 to planar base 1107.

The second heat exchanger 1101 may comprise a heat sink 1003. The heat sink 1003 may have a planar metal base 1102 in direct thermal contact with the upper major surface 1104 of the cooling modules 1009, 1009', 1009", and a plurality of planar metal fins 1108 extending substantially perpendicular to the base 1102 and vertically upward away from the liquid heat exchanger blocks 1010, 1010', 1010". Heat may be conducted between modules 1009, 1009', 1009" and external heat sink 1101 and transferred between heat sink 1101 and a surrounding environment. Electric case fans 1002, 1002', 1002" may be operatively connected to the power supply/main control board 1004 and mounted inside the housing 903 adjacent respective heat sink 1003. The exemplary fans 1002, 1002', 1002" promote airflow across the sink fins 1002 and outwardly from the control unit 100 through perforations in the sides of the housing 903. In one embodiment, the heat sink 1003 may have a substantially larger base 1102 (as compared to the liquid heat exchanger blocks 1010, 1010', 1010") and a substantially large number of fins 1108 (e.g., 32 or more). Both liquid heat exchanger blocks and external heat sinks may be active or passive, and may be constructed of any suitable conductive material, including aluminum, copper, and other metals. The heat sinks may have a thermal conductivity of 400 watts per Kelvin per meter (W/mK), or more. The case fans 1002, 1002', 1002" may automatically activate and shut off as needed.

From the reservoir 1001, the temperature conditioned liquid may exit through outlet 1007 and enters the conduit assembly comprising an arrangement of in-housing Z-, L-, 7-, and S-shaped tubes 1007 (and joints). A pump 1008 may be operatively connected to the reservoir 1001 and function to circulate the liquid through the control unit 801 in a circuit including the in-housing tubes 1007 (and joints), flexible liquid supply line 903, silicone pad tubes 805, liquid return line 802, and back into the reservoir 1001 through liquid return 1008.

The exemplary temperature control unit 801 may further comprise other features and electronics not shown including a touch control and display board, overheat protectors, liquid level sensor, thermostat, additional case fans, and other such components. The control unit 801 may also comprise an external power cord designed to plug into standard household electrical outlets. The bed additionally or alternatively can include other animal interaction elements, such as, for example and without limitation, a soothing element (e.g., a massage pad, a rocker, etc.) that can be activated to sooth the animal (e.g., during times of detected stress/nervousness, crying, restlessness, etc.), an agitator or alarm that can be activated to prompt the animal to leave the bed (e.g., if a determination is made that the animal has been resting or inactive in the bed for an excessive amount of time). Temperature itself can be controlled to prompt the animal to leave the bed, e.g., making the bed too warm or too cold for comfort.

For the purposes of describing and defining the present invention, it is noted that the use of relative terms, such as "substantially", "generally", ⊗approximately, and the like, are utilized herein to represent an inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While only a few embodiments of the present disclosure have been shown and described, it will be obvious to those skilled in the art that many changes and modifications may be made thereunto without departing from the spirit and scope of the present disclosure as described in the following claims.

The methods and systems described herein may be deployed in part or in whole through a machine that executes computer software, program codes, and/or instructions on a processor. The present disclosure may be implemented as a method on the machine, as a system or apparatus as part of or in relation to the machine, or as a computer program product embodied in a computer readable medium executing on one or more of the machines. In embodiments, the processor may be part of a server, cloud server, client, network infrastructure, mobile computing platform, stationary computing platform, or other computing platforms. A processor may be any kind of computational or processing device capable of executing program instructions, codes, binary instructions and the like, including a central processing unit (CPU), a general processing unit (GPU), a logic board, a chip (e.g., a graphics chip, a video processing chip, a data compression chip, or the like), a chipset, a controller, a system-on-chip (e.g., an RF system on chip, an AI system on chip, a video processing system on chip, or others), an integrated circuit, an application specific integrated circuit (ASIC), a field programmable gate array (FPGA), an approximate computing processor, a quantum computing processor, a parallel computing processor, a neural network processor, or other type of processor. The processor may be or may include a signal processor, digital processor, data processor, embedded processor, microprocessor or any variant such as a co-processor (math co-processor, graphic co-processor, communication co-processor, video co-processor, AI co-processor, and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more threads. The thread may spawn other threads that may have assigned priorities associated with them; the processor may execute these threads based on priority or any other order based on instructions provided in the program code. The processor, or any machine utilizing one, may include non-transitory memory that stores methods, codes, instructions and programs as described herein and elsewhere. The processor may access a non-transitory storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache, network-attached storage, server-based storage, and the like.

A processor may include one or more cores that may enhance speed and performance of a multiprocessor. In embodiments, the process may be a dual core processor, quad core processors, other chip-level multiprocessor and the like that combine two or more independent cores (sometimes called a die).

The methods and systems described herein may be deployed in part or in whole through a machine that executes computer software on a server, client, firewall, gateway, hub, router, switch, infrastructure-as-a-service, platform-as-a-service, or other such computer and/or networking hardware or system. The software may be associated with a server that may include a file server, print server, domain server, internet server, intranet server, cloud server, infrastructure-as-a-service server, platform-as-a-service server, web server, and other variants such as secondary server, host server, distributed server, failover server, backup server, server farm, and the like. The server may include one or more of memories, processors, computer readable media, storage media, ports (physical and virtual), communication devices, and interfaces capable of accessing other servers, clients, machines, and devices through a wired or a wireless medium, and the like. The methods, programs, or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers, social networks, and the like. Additionally, this coupling and/or connection may facilitate remote execution of programs across the network. The networking of some or all of these devices may facilitate parallel processing of a program or method at one or more locations without deviating from the scope of the disclosure. In addition, any of the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

The software program may be associated with a client that may include a file client, print client, domain client, internet client, intranet client and other variants such as secondary client, host client, distributed client and the like. The client may include one or more of memories, processors, computer readable media, storage media, ports (physical and virtual), communication devices, and interfaces capable of accessing other clients, servers, machines, and devices through a wired or a wireless medium, and the like. The methods, programs, or codes as described herein and elsewhere may be executed by the client. In addition, other devices required for the execution of methods as described in this application may be considered as a part of the infrastructure associated with the client.

The client may provide an interface to other devices including, without limitation, servers, other clients, printers, database servers, print servers, file servers, communication servers, distributed servers and the like. Additionally, this coupling and/or connection may facilitate remote execution of programs across the network. The networking of some or all of these devices may facilitate parallel processing of a program or method at one or more locations without deviating from the scope of the disclosure. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The methods and systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements. The methods and systems described herein may be adapted for use with any kind of private, community, or hybrid cloud computing network or cloud computing environment, including those which involve features of software as a service (SaaS), platform as a service (PaaS), and/or infrastructure as a service (IaaS).

The methods, program codes, and instructions described herein and elsewhere may be implemented on a cellular network with multiple cells. The cellular network may either be frequency division multiple access (FDMA) network or code division multiple access (CDMA) network. The cellular network may include mobile devices, cell sites, base stations, repeaters, antennas, towers, and the like. The cell network may be a GSM, GPRS, 3G, 4G, 5G, LTE, EVDO, mesh, or other network types.

The methods, program codes, and instructions described herein and elsewhere may be implemented on or through mobile devices. The mobile devices may include navigation devices, cell phones, mobile phones, mobile personal digital assistants, laptops, palmtops, netbooks, pagers, electronic book readers, music players and the like. These devices may include, apart from other components, a storage medium such as flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer-to-peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g., USB sticks or keys), floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, network-attached storage, network storage, NVME-accessible storage, PCIE connected storage, distributed storage, and the like.

The methods and systems described herein may transform physical and/or intangible items from one state to another. The methods and systems described herein may also transform data representing physical and/or intangible items from one state to another.

The elements described and depicted herein, including in flow charts and block diagrams throughout the figures, imply logical boundaries between the elements. However, according to software or hardware engineering practices, the depicted elements and the functions thereof may be implemented on machines through computer executable code using a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices, artificial intelligence, computing devices, networking equipment, servers, routers and the like. Furthermore, the elements depicted in the flow chart and block diagrams or any other logical component may be implemented on a machine capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described above, and steps associated therewith, may be realized in hardware, software or any combination of hardware and software suitable for a particular application. The hardware may include a general-purpose computer and/or dedicated computing device or specific computing device or particular aspect or component of a specific computing device. The processes may be realized in one or more microprocessors, microcontrollers, embedded microcontrollers, programmable digital signal processors or other programmable devices, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine-readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions. Computer software may employ virtualization, virtual machines, containers, dock facilities, portainers, and other capabilities.

Thus, in one aspect, methods described above and combinations thereof may be embodied in computer executable code that, when executing on one or more computing devices, performs the steps thereof. In another aspect, the methods may be embodied in systems that perform the steps thereof and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

While the disclosure has been disclosed in connection with the preferred embodiments shown and described in detail, various modifications and improvements thereon will become readily apparent to those skilled in the art. Accordingly, the spirit and scope of the present disclosure is not to be limited by the foregoing examples, but is to be understood in the broadest sense allowable by law.

The use of the terms "a" and "an" and "the" and similar referents in the context of describing the disclosure (especially in the context of the following claims) is to be construed to cover both the singular and the plural, unless otherwise indicated herein or clearly contradicted by context. The terms "comprising," "with," "including," and "containing" are to be construed as open-ended terms (i.e., meaning "including, but not limited to,") unless otherwise noted. Recitations of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. The term "set" may include a set with a single member. No language in the specification should be construed as indicating any non-claimed element as essential to the practice of the disclosure.

While the foregoing written description enables one skilled to make and use what is considered presently to be the best mode thereof, those skilled in the art will understand and appreciate the existence of variations, combinations, and equivalents of the specific embodiment, method, and examples herein. The disclosure should therefore not be limited by the above described embodiment, method, and examples, but by all embodiments and methods within the scope and spirit of the disclosure.

All documents referenced herein are hereby incorporated by reference as if fully set forth herein.

Various embodiments of the present invention may be characterized by the potential claims listed in the paragraphs following this paragraph (and before the actual claims provided at the end of the application). These potential claims form a part of the written description of the application. Accordingly, subject matter of the following potential claims may be presented as actual claims in later proceedings involving this application or any application claiming priority based on this application. Inclusion of such potential claims should not be construed to mean that the actual claims do not cover the subject matter of the potential claims. Thus, a decision to not present these potential claims in later proceedings should not be construed as a donation of the subject matter to the public. Nor are these potential claims intended to limit various pursued claims.

Without limitation, potential subject matter that may be claimed (prefaced with the letter "P" so as to avoid confusion with the actual claims presented below) includes:

P1. Smart animal beds of the types disclosed herein.

P2. Smart animal food dispensers of the types disclosed herein including handling of food containers/pods for dispensing food, monitoring animal food intake, and handling of used containers/pods.

P3. Animal food containers/pods of the types disclosed herein for use with smart animal food dispensers including features allowing the containers/pods to be opened at time of dispensing and closed or covered during collection back into the smart animal food dispenser.

P4. Smart water dispensers of the types disclosed herein.

P5. Smart animal collars of the types disclosed herein including smart animal collars with energy harvesting system for power.

P6. Energy harvesting system for use with smart animal collars or more generally for other types of products, both animal/pet-related (e.g., smart pet toys) and not animal/pet-related products.

P7. A platform that communicates with one or more smart animal products including one or more of a smart animal bed, smart animal food dispenser, smart water dispenser, and/or smart animal collar and receives information from such product(s) and controls such product(s) including coordination across multiple products (e.g., determining an amount of food and/or water to dispense based on animal activity levels ascertained from motion sensing data from a smart animal collar and/or smart animal bed.

Additional embodiments may be disclosed and claimed. What is claimed is:

1. A smart animal bed system comprising:
a base having a padded animal bed;
at least one sensor for providing sensor signals indicative of a condition of an animal within the padded animal bed; and
a temperature control system having a heating mode and a cooling mode operated by a controller, wherein the controller is configured to:
determine a condition of the animal based on the sensor signals, the condition including at least one of resting time or inactivity time;
measure an activity level for the animal over a specified time period based at least in part on the determined condition of the animal;
comparing the measured activity level for the animal to recommended activity level(s) for the animal; and
determining to prompt the animal to leave the padded animal bed based on the measured activity level for the animal relative to the recommended activity level(s) for the animal,
said prompting including selecting one of the heating mode or the cooling mode for changing temperature of the padded animal bed; and
activating the selected mode of the temperature control system to change the temperature of the padded animal bed to prompt the animal to leave the padded animal bed.

2. A smart animal bed system according to claim 1, wherein the at least one sensor comprises a piezoelectric sensor.

3. A smart animal bed system according to claim 1, wherein the temperature control system comprises a thermally conductive gel-padded surface coupled to a heat sink.

4. A smart animal bed system according to claim 3, wherein the thermally conductive gel-padded surface is affixed to a thermally conductive baseplate, and wherein the thermally conductive baseplate is coupled to the heat sink.

5. A smart animal bed system according to claim 4, wherein the thermally conductive baseplate is coupled to the heat sink via a set of thermoelectric heat pump devices, wherein each thermoelectric heat pump device is in low-thermal-resistance contact with the baseplate and the heat sink.

6. A smart animal bed system according to claim 5, wherein each thermoelectric heat pump device is in low-thermal-resistance contact with the base plate and the heat sink via a debossed pad.

7. A smart animal bed system according to claim 6, where the debossed pad is configured to accommodate a thermal insulator beneath the thermally conductive baseplate.

8. A smart animal bed system according to claim 5, wherein current flow through the thermoelectric heat pump devices in a first direction provides cooling and wherein current flow through the thermoelectric heat pump devices in a reverse direction provides heating such that the controller is configured to switch between the heating mode and the cooling mode by switching the current flow direction.

9. A smart animal bed system according to claim 8, further comprising a power source for providing the current flow.

10. A smart animal bed system according to claim 5, wherein the thermoelectric heat pump devices are Peltier devices.

11. A smart animal bed system according to claim 4, further comprising at least one fan for drawing heat from the heat sink.

12. A smart animal bed system according to claim 4, wherein the thermally conductive baseplate includes a thermal insulator.

13. A smart animal bed system according to claim 12, wherein the thermal insulator comprises foam insulation.

14. A smart animal bed system according to claim 1, wherein the temperature control system comprises at least one conduit through which heated fluid is circulated in the heating mode and through which cooled fluid is circulated in the cooling mode.

15. A smart animal bed system according to claim 14, further comprising a liquid reservoir for holding liquid to be heated or cooled.

16. A smart animal bed system according to claim 14, further comprising:

a thermoelectric element for selectively heating and cooling the liquid.

17. A smart animal bed system according to claim 14, further comprising at least one conduit through which the fluid is circulated through a thermally regulated zone of the padded animal bed.

18. A smart animal bed system according to claim 17, further comprising a pump for circulating the fluid through the at least one conduit.

19. A smart animal bed system according to claim 1, further comprising an agitator or alarm that can be activated by the controller.

20. A smart animal bed system according to claim 1, further comprising a soothing element that can be activated by the controller.

21. A smart animal bed system according to claim 1, further comprising:

an ambient temperature sensor for providing ambient temperature signals, wherein the controller is configured to selectively provide heating or cooling to the padded animal bed based at least in part on the condition and the ambient temperature signals.

22. A smart animal bed system according to claim 1, wherein the controller is integral to the base having the padded animal bed.

23. A smart animal bed system according to claim 1, wherein the controller is separate from the base having the padded animal bed, the controller receiving the sensor signals over a communication system and providing control signals to the temperature control system over the communication system.

24. A smart animal bed system according to claim 23, wherein the controller is a cloud-based controller.

25. A smart animal bed system according to claim 23, wherein the communication system comprises the Internet.

\* \* \* \* \*